(12) United States Patent
Couraud et al.

(10) Patent No.: US 8,084,254 B2
(45) Date of Patent: Dec. 27, 2011

(54) HUMAN BLOOD BRAIN BARRIER MODEL

(75) Inventors: Pierre-Olivier Couraud, Auffargis (FR); Ignacio Romero, London (GB); Babette Weksler, Tenafly, NJ (US)

(73) Assignees: Institut National de la Sante et de la Recherche Medicale (INSERM), Paris (FR); Cornell Research Foundation, Inc., Ithaca, NY (US)

( * ) Notice: Subject to any disclaimer, the term of this patent is extended or adjusted under 35 U.S.C. 154(b) by 674 days.

(21) Appl. No.: 11/720,144

(22) PCT Filed: Nov. 29, 2005

(86) PCT No.: PCT/IB2005/003574
§ 371 (c)(1),
(2), (4) Date: Nov. 28, 2008

(87) PCT Pub. No.: WO2006/056879
PCT Pub. Date: Jun. 1, 2006

(65) Prior Publication Data
US 2010/0233750 A1    Sep. 16, 2010

Related U.S. Application Data

(60) Provisional application No. 60/631,230, filed on Nov. 29, 2004.

(51) Int. Cl.
*C12N 5/071* (2010.01)
*C12N 5/16* (2010.01)
(52) U.S. Cl. .................. 435/366; 435/325; 424/93.7
(58) Field of Classification Search .................. None
See application file for complete search history.

(56) References Cited

U.S. PATENT DOCUMENTS
6,093,553 A    7/2000  Yazdanian et al.

OTHER PUBLICATIONS

Gu Xiaolin et al, "Brian and retinal vascular endothelial cells with extended life span established by ectopic expression of telomerase", Jul. 2003, pp. 3219-3225, vol. 44, No. 7, IOVS.
Muruganandam et al, "Development of Immortalized Human Cerebromicrovascular Endothelial Cell Line as an in vitro model of the human blood-brain barrier", Oct. 1997, pp. 1187-1197, vol. 11, No. 13, FASEB Journal, Fed. Of American Soc. For Experimental Biology, Bethesda, MD, USA.
Couraud et al, "Development and characterization of immortalized cerebral endothelial cell lines", 2003, p. 349-364, vol. 89, Methods in Molecular Medicine, Humana Press, Inc., Totowa, New Jersey.

*Primary Examiner* — Laura Schuberg
(74) *Attorney, Agent, or Firm* — B. Aaron Schulman, Esq.; Terry L. Wright, Esq.; Stites & Harbison, PLLC (57) ABSTRACT

The present invention relates to an immortalized human brain endothelial cell line that is useful as an in vitro model of the blood brain barrier.

5 Claims, 8 Drawing Sheets

HUMAN BLOOD BRAIN BARRIER MODEL

This application claims benefit of U.S. Provisional Application No. 60/631,230, filed Nov. 29, 2004 (which is hereby incorporated by reference).

The present invention relates to an immortalized human brain endothelial cell line that is useful as an in vitro model of the blood brain barrier.

Endothelial cells that line the microvasculature of the central nervous system (CNS) differ fundamentally from other vascular endothelia in their capacity to regulate the passage of molecules and cells to and from the neural parenchyma. This selectivity resides in specialized features unique to CNS endothelia, including expression of tight intercellular junctions that markedly limit paracellular permeability plus a unique pattern of receptors, transporters and non-selective drug export pumps that protect the CNS from a very large variety of potentially harmful hydrophobic compounds. Together, these structural and physiologic specializations constitute the blood brain barrier (BBB).

The BBB lies at a critical interface between the CNS and the rest of the organism that is central to the maintenance of normal neuronal function. Because of the importance of this structure, the unique properties of CNS endothelial cells have been widely investigated, particularly as altered BBB function is often thought to play a central role in the pathogenesis of various CNS diseases, and has been directly implicated in the pathological changes observed in multiple sclerosis or Alzheimer's disease. Although much has been learnt from in vivo studies, the limitations imposed by whole animal experiments has led to the development of techniques to isolate and culture CNS-derived endothelial cells from various species (Joo, 1993). Unfortunately, these cultured endothelial cells usually fail to develop functional tight junctions. A co-culture system has been developed in which brain endothelial cells are grown on microporous filter membrane inserts in the presence of primary cultures of astrocytes in order to mimic the anatomical and functional relationship between brain endothelium and surrounding astrocyte foot processes (Rubin et al. 1991; Cecchelli et al. 1999). Up to the present time co-cultures have essentially been achieved from bovine brain, where measures of in vitro permeability of standard molecules correlate well and over a wide range of hydrophilicity with the in vivo cerebral bio-availability of the same molecules (Cecchelli et al. 1999). Several models of bovine immortalized brain endothelial cells have thus been described (U.S. Pat. No. 6,093,553; Gumbleton and Audus, 2001). In addition, mono-cultures of porcine brain endothelial cells have also been proposed as an alternative BBB model (Engelbertz et al. 2000). While such models are of value for both drug screening and basic studies on BBB biology, their use for immunological studies remains difficult because of lack of appropriate molecular tools. In particular, the absence to date of a human model hampers any investigations on the mechanisms of infiltration of human immune cells or human-specific viral or bacterial pathogens. In addition, species differences in the substrate specificity of drug export pumps was previously reported (Yamazaki et al. 2001; Schwab et al. 2003), highlighting the need of an in vitro model of human BBB for the predictive assessment of candidate drug permeability across the BBB in humans.

Although primary cultures of human brain endothelial cells have been shown to retain some characteristics of brain endothelium phenotype (Dorovini-Zis et al. 1991) (Biegel et al. 1995), upon even limited passaging, they rapidly undergo senescence and de-differentiation, thus hampering their usefulness as in vitro models of human BBB.

Attempts have been made to develop immortalized human brain endothelial cell lines, without much success so far (Zhang et al., 2003; Prudhomme et al., 1986; Safaa Ibrahim et al., 2000) or with a very limited phenotypic characterization that prevents any conclusion on their potential applications (Stins et al. 1997) (Gu et al. 2003).

The inventors have now produced and extensively characterized an immortalized human brain endothelial cell line.

This cell line was designated hCMEC/D3 and deposited under Budapest Treaty at CNCM (Collection Nationale de Cultures de Microorganismes) (Institut Pasteur) on Oct. 7 2004, under number I-3308.

This cell line is derived from a primary cell culture through coexpression of the catalytic subunit of telomerase (hTERT) and the SV40 large T antigen via a highly efficient, lentiviral vector system. This cell line stably retains morphological characteristics of primary brain endothelial cells and expresses specific brain endothelial markers and cell surface adhesion molecules. Moreover, hCMEC/D3 cells display highly restricted paracellular permeability to hydrophilic molecules and to several standard compounds over a wide range of hydrophobicity that can be correlated to their in vivo brain perfusion capacity. This cell line further expresses the functional multidrug resistance proteins known to be expressed at the BBB.

The inventors report here an immortalized human endothelial cell line derived from brain microvasculature. The strategy used to produce the hCMEC/D3 cell line was designed on the basis of inserting human telomerase to prolong stable, lifespan of differentiated cells in culture as well as SV40 T antigen to foster proliferation. The results obtained by the inventors constitute an extensive phenotypic characterisation of an immortalised human brain microvascular endothelial cell line which stably maintains in culture most of the unique structural and biochemical properties of brain endothelium in vivo. In addition, the restricted permeability of monolayers of these endothelial cells to macromolecules demonstrates functional retention in vitro of physiological properties of the BBB. Unlike primary cultures of CNS-derived endothelia which are difficult to obtain pure, are phenotypically unstable, and rapidly undergo cellular senescence after a limited number of divisions, this immortalized clonal cell line showed no indications of phenotypic drift or decrease in the rate of population doubling over the generation of 35 passages (over 100 population doublings). The hCMEC/D3 cell line exhibited a non-transformed phenotype, on the basis of the following observations: (i) cells maintain elongated morphology and the capacity to form contact-inhibited monolayers characteristic of the primary brain endothelial cells from which they were derived, (ii) cell proliferation is dependent upon the presence of appropriate substrate and serum components, (iii) the cells do not form foci of multilayered cells, do not proliferate in soft agar, but rather form vascular cords within three-dimensional reconstituted extracellular matrix (Matrigel®), (iv) they retain a female, diploïd karyotype. Moreover, the hCMEC/D3 cell line stably retains a physiologically normal endothelial phenotype, as indicated by the continued expression of a number of endothelial markers, including: von Willebrand factor, PECAM-1, VE-cadherin and ICAM-2 together with the appropriate upregulation of activation markers upon exposure to inflammatory stimuli.

The tight junctions of the BBB are the major contributor to the extremely low permeability to both solutes and cells. Junctional expression of claudins and occludin, the integral membrane components of tight junctions, as well as continuous junctional expression of ZO-1, when expressed all together are reported to correlate in situ with functional tight junctions (Tsukita and Furuse 1999; Wolburg and Lippoldt 2002; Wolburg et al. 2003). In terms of the relative contribution of these proteins to tight junction formation, it is of interest to note that, although occludin unexpectedly appear to be dispensable (Saitou et al. 1998), loosening of the BBB was reported in claudin-5-deficient mice (Nitta et al. 2003), highlighting the key contribution of this adhesion molecule to BBB integrity. hCMEC/D3 cells display a generally continuous junctional expression of ZO-1 and JAM-A. Junctional expression of the tight junction-specific integral membrane proteins claudin-5 was also observed. Claudin-1, which is not expressed at the BBB, could not be detected in hCMEC/D3 cells. Demonstration of occludin was less consistently detected at cell-cell contacts than other tight junctional markers. Altogether, these results are consistent with the maintenance by hCMEC/D3 cells of the overall tight junction organization.

This conclusion is supported by the permeability results: hCMEC/D3 cell monolayers display a highly restricted permeability to standard drugs over a wide range of hydrophobicity, in good correlation with in vivo permeability values from brain perfusion studies in adult rats. These data, obtained with a variety of different compounds, clearly indicate that the hCMEC/D3 cell monolayers, even in the absence of co-culture, possess intercellular junctions that are much tighter than those in previously immortalized rat brain endothelial cell lines (RBE4, GPNT cell lines) (Rist et al. 1997; Romero et al. 2000). Furthermore, paracellular permeability of inulin across hCMEC/D3 cell monolayers was similar to that measured in the reference in vitro model based on bovine brain endothelial cells in co-culture with primary rat astrocytes (Cecchelli et al. 1999). However, sucrose permeability was higher than in the reference model and TEER values were constantly very low. Altogether, these results demonstrate that hCMEC/D3 cell monolayers constitute a valuable in vitro model of human BBB which mimics brain endothelium restricted permeability for a wide variety of compounds.

Among the seven identified subfamilies of the ABC superfamily in humans, consisting of more than 40 known members, three subfamilies (B, C and G) contain efflux transporters that are expressed and active at the BBB. P-gp (or ABCB1) and the recently identified BCRP (or ABCG2) are inserted into the luminal cell membrane of brain endothelial cells and thus constitute a first line of defense against substrate penetration into brain (Begley 2004). Among the seven members of the MRP family, MRP1 has been suggested to be abluminally expressed by brain endothelium, at a very low level in situ or in freshly isolated brain endothelial cells, at a much higher level in cultured cells, including rat and human brain endothelial cells (Seetharaman et al. 1998; Gutmann et al. 1999); in addition, other members, MRP2, MRP5, with some species variations, were shown to be expressed by brain endothelial cells (Begley 2004; Berezowski et al. 2004). Altogether, these ABC efflux transporters contribute to the multidrug resistance phenomenon at the BBB. It was herein demonstrated that at least P-gp, MRP1 and BCRP are functionally expressed in hCMEC/D3 cells, as they are in vivo at the BBB. In addition, MRP5 transcript was also detected.

Considering the previously reported species difference in P-gp substrate specificity (Yamazaki et al. 2001; Schwab et al. 2003), availability of this cell line may significantly increase the predictability of in vivo results in humans, regarding BBB permeability to lipid soluble molecules.

The hCMEC/D3 cell line exhibits the phenotypic characteristics of the BBB without the need of any coculture with glial cells.

Nevertheless, one may also culture the hCMEC/D3 cells with glial cells, to increase the functional expression of P-gp and other ABC efflux transporters and to potentially improve tight junction organization (with occludin expressed at cellular junctions).

The hCMEC/D3 cell line is useful as an in vitro model of human BBB. The model allows for testing the access of potential new therapeutics to the brain parenchyma. For example, drugs such as L-DOPA can cross the BBB, being recognized and transported by amino acid transporters. Lipophilic drugs are also able to penetrate the BBB, except those which are substrates of ABC transporters and are then pumped out of the brain by these efflux pumps. However, potentially therapeutic drugs that are not lipophilic and for which no specific transport mechanism exists may be unable to penetrate the BBB or may do so at rates insufficient to maintain a therapeutic drug level in the brain.

It is therefore also an object of the present invention to provide a method of measuring blood brain barrier permeability of a test substance. Such method comprises:

providing hCMEC/D3 cells in one or more confluent monolayer(s);

contacting (i.e. incubating) said test substance with the confluent monolayer(s); and measuring the amount of said test substance permeated across the confluent monolayer(s).

The cells are grown to confluency, preferably on a porous substratum-coated solid support, e.g., semi-permeable filters or membranes. Endothelial cells can attach to and grow on Nucleopore polycarbonate filters (Costar, Inc., Cambridge, Mass.), Millicell CM and HA porous nitrocellulose filters (Millipore Corp, Bedford, Mass.), and collagen membranes (ICN Biomedical, Inc., Costa Mesa, Calif.). Nucleopore filters promote media exchange across the filter. These two-chamber systems are known to permit endothelial cells to fully differentiate and to polarize, with the apical plasma membrane facing the upper compartment (figuring the blood compartment in vivo) and the basal plasma membrane attached to the filter, facing the lower compartment (figuring the brain compartment in vivo).

The test substance may be any synthetic or natural compound or mixtures thereof. In particular, it may be a low molecular weight hydrophilic or lipophilic pharmaceutical or drug candidate.

The method of the invention can measure passive diffusion or active transport and in addition can be varied, as appreciated by those skilled in the art, to perform characteristic measurements such as carrier mediated transport wherein permeability values are measured as a function of concentration of the solute. Efflux transport can be measured wherein measuring permeability values is performed in the presence or absence of inhibitors of the efflux pumps such as, but not limited to, cyclosporin-A, PSC-833, MK-571, KO-143. The methods of the present invention can also be used to measure blood brain barrier metabolism of a substance by measuring permeability values and profiling the metabolic degradation of compounds of interest as a function of time using quantitative analytical techniques such as high pressure liquid chromatography and mass spectrometry. Test substances that prove to pass the hCMEC/D3 cells used as blood brain barrier model may be further analyzed for their pharmacological profile.

In addition to the measurement of blood brain barrier permeability, the hCMEC/D3 cells are useful in a variety of other tests and analysis in the field of pharmacology.

For instance, the hCMEC/D3 cells may be used in a method for determining the toxicity of a test substance towards the blood brain barrier, which method comprises contacting (i.e. incubating) the test substance with the hCMEC/D3 cells and assessing the viability of the cells.

A range of concentrations of the test substance is generally employed. The skilled person is familiar with various standard methods for assessing cell viability, such a a MTT cell viability assay. The yellow tetrazolium MTT (3-(4, 5-dimethylthiazolyl-2)-2,5-diphenyltetrazolium bromide) is reduced by metabolically active cells, in part by the action of dehydrogenase enzymes, to generate reducing equivalents such as NADH and NADPH. The resulting intracellular purple formazan can be solubilized and quantified by spectrophotometric means.

Cell membrane damage may also be evaluated, by performing lactate dehydrogenase assay for example. For cell differentiation evaluation, cell morphology and changed distribution of differentiation-specific protein marker may be analyzed. For cell replication and growth evaluation, BrdU assay may be performed.

The hCMEC/D3 cells are also of great interest in designing viral, chemical, peptidic or any vector for drug targeting or delivery to the brain.

In that prospect, one may use a vector that expresses a protein with high specificity for brain endothelium. The hCMEC/D3 cell line may be employed to test whether the protein actually targets the cell lines, and to optimize the binding and internalization of said vector.

In addition, since Aβ expresses a wide variety of adhesion molecules and receptors of immunomodulatory factors, the hCMEC/D3 cell line may be useful for studying the interaction with deleterious activated autoreactive leukocytes which are known to be involved in the progression of neuroinflammatory and/or demyelinating diseases.

The observation that vascular dysfunction in brains of individuals with Alzheimer's disease contributes to the severity of the disease led to the hypothesis that the neurodegeneration might be a consequence of altered drug transport across the BBB and abnormal cerebral blood flow evoked by amyloid peptide (Aβ) deposition. In addition, it has been proposed that transport of Aβ between the brain, blood and cerebrospinal fluid, and across the BBB, regulates brain Aβ (Zlokovic, 2004). The low-density lipoprotein receptor-related protein (LRP), a member of the LDL receptor family, expressed on the abluminal membrane of brain endothelial cells, is known to regulate Aβ clearance by controlling its efflux from brain to blood via transport across the BBB. Accordingly, drugs that increase the LRP-mediated Aβ trans-endothelial transport towards plasma and thus decrease Aβ accumulation in the brain parenchyma would be useful in treating Alzheimer's disease. The hCMEC/D3 cell line may be very useful for testing and optimizing these drug candidates.

The figures and examples below illustrate the invention without limiting its scope.

EXAMPLES

Materials and Methods

Materials

EBM-2 medium was from Clonetics (Cambrex Bio-Science, Wokingham, UK) and was supplemented with VEGF, IGF-1, EGF and basic FGF, hydrocortisone, ascorbate, gentamycin and 2.5% fetal bovine serum (FBS) recommended by the manufacturer: this fully supplemented medium is designated as Microvascular Endothelial Cell Medium-2 (EGM™-2 MV). Collagen type I was obtained from BD Biosciences Pharmingen (Le Pont de Claix, France).

Human recombinant IFN-γ was obtained from Genzyme (Cambridge, Mass., USA). Human TNF-α, anti-human platelet endothelial cell adhesion molecule-1 (PECAM-1, clone 9G11), anti-DC-SIGN-1 (EAH01), -DC-SIGN-2 (120612) monoclonal antibodies were obtained from R&D systems (Abingdon, Oxon, UK). Mouse anti-intercellular adhesion molecule-1 (ICAM-1, clone HA-58), anti-vascular cell adhesion molecule 1 (VCAM-1, clone 51-10C9) monoclonal antibodies were from BD Biosciences. Mouse anti ICAM-2 (CBR-IC2/2) monoclonal antibody and rabbit anti-VE-Cadherin polyclonal antibodies were obtained from Bender Medsystems. Rabbit anti-human von-Willebrand factor polyclonal antibody was obtained from Dako (Oxford, UK). Polyclonal anti-ZO-1, anti-occludin, anti-claudin-1, claudin-3, claudin-5 antibodies and monoclonal anti-occludin antibodies were obtained from Zymed (San Fransisco, Calif., USA). Monoclonal antibodies against β- and γ-catenins were obtained from Transduction Laboratories (Lexington, Ky., USA). Monoclonal anti-CD40 (EA-5) antibody, anti-human MRP-1 (QCRL-1), anti-human BCRP, anti-human P-glycoprotein (C219) antibodies were all from Calbiochem Merck Biosciences Nottingham, UK), monoclonal anti-SV40-T antigen and anti-h-TERT antibodies were from Santa Cruz (Santa Cruz, Calif., USA). Monoclonal anti-JAM-A antibody was kindly provided by Dr E. Dejana (Instituto Mario Negri, Milano, Italy). Monoclonal anti-MHC-II, Cy-2, Cy-3, TRITC or FITC-conjugated secondary antibodies were obtained from Jackson Immunoresearch (PA, USA). [$^{14}$C]- or [$^3$H]-radiolabelled sucrose, inulin, imipramine, diazepam, prazosin, colchicine, vincristine, morphine-6-glucuronide- and daunorubicin were obtained from Amersham (Les Ulis, France). Calcein-acetoxymethylester (calcein-AM) was from Molecular Probe. Rhodamine 123, recombinant human bFGF, FITC or TRITC-conjugated phalloidin and all other reagents were obtained from Sigma (St Quentin Fallavier, France), unless otherwise specified.

Isolation of Human Brain Endothelial Cells

Human brain tissue was obtained following surgical excision of an area from the temporal lobe of an adult female with epilepsy carried out at Kings College Hospital, London in accordance with the guidelines of the Local Ethics Committee and research governance guidelines. The isolation procedure closely follows that of Abbott et al. for primary rat brain endothelial cells (Abbott et al. 1992), with minor modifications. Brain tissue was freed of meninges and surface vessels and was finely chopped and dispersed by enzymatic digestion in collagenase/dispase (1 mg/ml), DNAse I (20 U/ml) and tosyl-lysyl-chloro-methylketone (0.15 μg/ml) solution in Ca- and Mg-free HBSS for 1 h at 37° C. Microvessel fragments were separated from other material and single cells by density dependent centrifugation on 25% bovine serum albumin (BSA). The floating single cell layer was used to isolate primary astrocytes as previously described (Flynn et al. 2003). The pelleted microvascular fraction was subjected to a second digest in collagenase/dispase solution at 37° C. for 2 h. The microvessel fragment suspension was then centrifuged over a pre-formed 50% Percoll gradient. The microvessel fragments were washed and plated onto Type I collagen-coated plastic tissue culture flasks in EGM™-2 MV growth medium containing FBS and growth supplements as indicated above. In order to eliminate non-endothelial cells with low levels of P-glycoprotein (P-gp) expression that are sensitive to puromycin cytotoxicity, puromycin (2 μg/ml) was added to the culture medium for the first three days following isolation. This procedure resulted in more than 95% pure endothelial cultures as assessed by morphological criteria and by expression of von Willebrand factor and other endothelial-specific markers (see Results section). The cultures were maintained at 37° C. in 5% $CO_2$ and EGM™-2 MV medium was replaced every 3 days until 50% confluence when they were used for lentiviral transduction or RT-PCR analysis (see below).

Immortalization and Selection of Human Brain Endothelial Cells

The immortalization of human brain endothelial cells was performed via sequential lentiviral transduction of hTERT and SV40 large T antigen into a primary culture of adult brain endothelial cells. Subconfluent cells at passage 0 were first incubated overnight with a low concentration of a highly efficient DNA flap lentiviral vector (Zennou et al. 2000) encoding hTERT (final concentration 100 ng p24 units/ml) in EGM-2 medium. Cells were then washed and left to grow for 1-2 days. This was followed by another overnight incubation with a low concentration of a DNA flap lentiviral vector encoding SV40-T antigen (20 ng p24 units/ml). Individual transduced cells were then isolated in the first subsequent passage by two rounds of limiting dilution cloning which produced several hundred proliferating cell lines. Among several hundred proliferating cell lines, one clonal population, designated hCMEC/D3, was selected on the basis of its endothelial morphology, growth capacity, contact inhibition at confluence and stable expression of markers of a normal endothelial phenotype: von Willebrand factor and PECAM-1, in addition to β-catenin and ZO-1 whose expression is indicative of normally constituted intercellular junctions, as well as the transduced genes hTERT and nuclear SV40 T antigen. This cell line was routinely grown on Type I collagen-coated (0.15%) plates in EGM-2 medium. Differentiation and expression of junction-related proteins was favored at confluence by further culture in EBM-2 medium lacking added growth factors and containing 0.25% FBS and 1 μM dexamethasone. For safety reasons, transduced cells were tested for any production of retroviral particles, using a sensitive enzyme assay for p24: in the first and second passage, and both cells and conditioned media were negative.

Immunocytochemistry

Immunocytochemical studies were performed on both immortalized cells and the primary cultures from which they were derived. Cells were seeded onto Type I collagen-coated Thermanox chamber slides, Thermanox coverslips (Nunc LabTek, Gibco, Paisley, UK) or the centre of 35 mm plates and grown to confluence. For characterization of junctional proteins, confluent cells were washed, fixed for 10 min in 4% paraformaldehyde, washed three times in PBS, permeabilized for 10 min in 0.2% Triton X-100, re-washed and blocked in 3% BSA for 30 min. For other analyses, cells were fixed in 3.7% formaldehyde in PBS, permeabilized with ice-cold acetone or methanol, washed in PBS and blocked in 0.5% BSA before staining. In all cases, cells were then incubated for 2 h with relevant antibodies, washed extensively in PBS and then incubated with fluorophore-conjugated secondary antibody for 1 h, followed by extensive rinsing prior to mounting in Mowiol (10% Mowiol 4-88, Calbiochem). Omission of the primary antibody served as negative control. After mounting, the cells were observed and photographed using a fluorescence microscope or a confocal fluorescence microscope (Leica or Zeiss).

Flow Cytometry

Flow cytometry analysis of endothelial cells was performed on a FACScan (Becton-Dickinson FACScan, Oxford, UK) as previously described (Romero et al. 2000). After washing in cation-free HBSS, cells were detached with trypsin-EDTA and the trypsin neutralized with serum-containing culture medium. Cell suspensions were centrifuged for 5 min at 300×g and pellets were resuspended for fixation for 10 min in 4% paraformaldehyde in PBS. The fixed cells were washed, permeabilized for 1 min with 0.1% Triton X-100 in PBS and blocked in 10% goat serum in PBS for 30 min. Cell suspensions were incubated for 1 h on ice with primary antibodies against surface epitopes followed by a further 1 h incubation with FITC-conjugated goat anti-mouse antibodies in the presence of 20% normal human serum. After two washes, cells were resuspended in PBS and analyzed. Unstained cells were used to set the parameters, and cells stained with FITC-conjugated goat anti-mouse antibodies alone were used to set background level. A minimal acquisition of 500,000 cells per sample was used. Negative controls were carried out using isotype matched irrelevant antibodies in place of the primary antibody. Intracellular antigens were detected as described above following fixation in 4% paraformaldehyde, quenching in 0.1 M glycine, and permeabilization in 0.2% BSA and 0.05% saponin.

Matrigel and Soft Agar Assays

Confluent hCMEC/D3 cells were resuspended in fresh EGM-2 medium at 50-100,000 cells per ml and one ml aliquots were layered over a pre-formed gelled layer of 250 µl reconstituted basement matrix (Matrigel, BD Biosciences) in wells of a 48-well culture plate and incubated at 37° C. for 6-24 h. Development of capillary-like networks and tubular structures was observed and photographed under a phase-contrast microscope.

For evaluation of the capacity of cells for anchorage-independent growth in soft agar, hCMEC/D3 cells at 200-2000 cells per ml of EGM-2 medium were suspended in a final concentration of 0.37% agar in the same medium and layered over a coating of 0.5% solid agar in wells of 24-well tissue culture dishes using triplicate wells for each concentration. The plates were incubated in a 5% CO2 incubator at 37° C. for up to 4 weeks. Human highly malignant glioblastoma U87 cells were used as positive controls, as described (Murphy et al. 1992). Colonies forming in the soft agar were counted at weekly intervals in 5 microscopic fields per well.

RNA Extraction and RT-PCR

Total RNA was extracted from hCMEC/D3 and primary human brain endothelial cells using 2 ml Trizol reagent (Invitrogen, Paisley, UK) according to the manufacturer's instructions. The RNA pellet was washed in 70% ethanol, dissolved in DEPC water and digested with DNase (Promega) to remove any contaminating DNA. For reverse transcription (RT) a 20 µl reaction containing 1 µg of RNA was carried out using random hexamers and ImProm-II Reverse Transcriptase (Promega) in the presence of 20 U RNasin (Promega). Primer annealing was performed at 25° C. for 5 minutes and transcription was run at 40° C. for 1 h, followed by inactivation of the enzyme at 70° C. for 15 min.

Four-microliter aliquots of the RT reaction product were used for PCR analyses in a reaction mixture containing 10 mM Tris-HCl, 50 mM KCl, 1.5 mM $MgCl_2$, 0.2 mM dNTPs, 1 µM of sense and anti-sense primers and 1U Taq DNA polymerase in a total volume of 20 µl. Amplification was performed in an iCycler (Biorad) with an initial denaturation step at 94° C. for 5 min; 35 cycles of 94° C. for 45 s, 55° C. for 45 s and 72° C. for 1 min; and a final elongation step at 72° C. for 7 mins. The annealing temperature was reduced to 53° C. for MRP5. For semi-quantitative expression analysis a cyclophilin fragment was amplified simultaneously. The products from the PCR amplification were separated by electrophoresis on a 1% agarose gel, stained with ethidium bromide and visualised under UV light.

Western Blot

The expression of MRP1, P-gp and MDR1 in hCMEC/D3 was carried out by immunoblot analysis, as well as the expression of claudin-5, occludin and transferrin receptor. Antibodies against claudin-5, occludin and transferrin receptor were from Zymed (San Francisco, Calif., USA). Cells were scraped in 40 µl SDS sample buffer (125 mM Tris-HCl pH 6.8, 4% sodium dodecylsulfate, 5% glycerol, 50 mM dithiothreitol, 1 mM orthovanadate, 0.05 µg/ml bromophenol blue) at 4° C., and heated at 95° C. for 5-10 min. Cell lysates were then resolved by SDS-PAGE and proteins were electroblotted onto BA23 nitrocellulose membrane (Schleicher & Schuell, Keene, N.H., USA) at 0.15 mA overnight at 4° C. Membranes were blocked in 5% non-fat dried milk and 0.05% Tween 20 at room temperature, in PBS for 2 h. Membranes were washed and subsequently incubated with anti-human MRP-1 (QCRL-1), anti-human BCRP, or anti-human P-gp (C219) (all from Merck Biosciences Ltd, Nottingham, UK) for 2 h at room temperature. After extensive washing in PBS containing 0.05% Tween-20, membranes were with horseradish peroxidase-conjugated goat anti-mouse IgG (Pierce, Chester, UK) for 1 h at room temperature. Membranes were extensively washed in PBS containing 0.05% Tween-20 and immunoblots were visualised by enhanced chemiluminescence detection (ECL, Amersham, Bucks, UK).

Chemokine Release

Chemokine release into culture medium by hCMEC/D3 and primary human brain endothelial cells (HBEC) cells following stimulation by cytokines for 48 h was measured as follows. Supernatants from confluent hCMEC/D3 and HBEC monolayers were collected after 48 h stimulation with TNF-α (50 ng/ml), IFN-γ (100 ng/ml) and TGF-β (25 ng/ml) (Genzyme, Cambridge, Mass., USA) or a combination of them and assayed by sandwich ELISA (R&D Systems) for chemokine production. Results presented are the mean±S.D. of three different experiments for CXCL8 and CCL2, two for CXCL10 and CCL5. Significance was tested by ANOVA followed by a post hoc t-test for CXCL8 and CCL2, no statistical analysis could be performed for CXCL10 and CCL5 as the number of experiments was too small.

Permeability Studies

The permeability of hCMEC/D3 cell monolayers to molecules of different size was measured as described (Dehouck et al. 1992; Rist et al. 1997; Couraud et al. 2003) on Transwell-Clear™ (polyester, 12 mm diameter, pore size 0.4 µm, Corning, Brumath, France) insert filters or polycarbonate insert filters (pore size 3 Corning) in EBM-2 medium containing 10% FCS, 100 U/ml penicillin and 100 µg/ml streptomycin. HCMEC/D3 cells were seeded on the filters at a density of 2×$10^5$ cells/$cm^2$ in normal culture medium (EGM-2). [$^{14}$C]- or [$^3$H]-radiolabelled sucrose, inulin, imipramine, diazepam, prazosin, colchicine, vincristine and morphine-6-glucuronide (M6G) (0.8 µCi/ml) or FITC-labelled dextrans of molecular weight 4, 40 and 70 kDa (1-2 mg/ml) were then added to the upper chamber, and the inserts were transferred sequentially at 10 min intervals from well to well of a tissue culture plate containing the same volume of medium. All plates were kept at 37° C. At each time point, the lower chamber was sampled and the radioactivity or fluorescence that passed through the cell-covered inserts was determined using a p-scintillation counter (Pharmacia Wallac 1410) or a fluorescence multi-well plate reader (Wallac Victor™ 1420), respectively. The volume cleared was plotted against time and the slopes of the curves, fitted using linear least squares regression, were used to calculate the permeability coefficients (Pe) of the endothelial monolayer, as described (Dehouck et al. 1992): $1/PS=1/me-1/mf$ and $Pe=PS/s$, where me and mf are the slopes of the curves corresponding to endothelial cells on filters and to filters only, respectively. PS (clearance) is the permeability surface area product and s is the surface area of the filter (1 cm$^2$). For FITC-dextrans, control and test clearance values were corrected for the presence of unconjugated fluorescein as described (van Bree et al. 1988). Permeability coefficients were correlated to recently reported rat or mouse in situ brain perfusion values (Cisternino et al. 2001; Cisternino et al. 2003, Cisternino et al. 2004) expressed as Kin values ($\mu l\ s^{-1}\ g^{-1}$): $PS=-F\ Ln(1-E)$, with $E=Kin/F$, where E is the brain extraction and F is the blood flow ($\mu l\ s^{-1}\ g^{-1}$).

Transendothelial electrical resistance (TEER) of hCMEC/D3 monolayers on Transwell-Clear™ filters was measured using an Endohm 12 chamber and an Endohmeter (World Precision Instruments Inc., Sarasota, Fla., USA). The baseline resistance of ECM-coated inserts was always subtracted from the resistance obtained in the presence of the endothelial cultures. Primary cultures of rat brain endothelial cells were used as control.

Drug Accumulation Studies

Cellular uptake of the fluorescent P-glycoprotein (P-gp)/BCRP substrate rhodamine 123 (Nare et al. 1994), the P-gp/MRP-1 substrate calcein-acetoxymethylester (calcein-AM) (Feller et al. 1995) (Bauer et al. 2003) and the non-selective P-gp/MRP-1/BCRP substrate [$^3$H] daunorubicin was measured as described previously (Regina et al. 1999), with minor modifications. Confluent hCMEC/D3 cells, grown in 24-well plates, were washed three times with PBS and preincubated for 30 min at 37° C. in a shaking waterbath with culture medium with or without a P-gp, MRP-1 or BCRP selective inhibitor: respectively the cyclosporin A analogue PSC-833 (10 µM, a gift from Novartis), MK-571 (10-50 µM; a gift from Merck), KO-143, a tetracyclic analogue of the fungal toxin fumitremorgin C (1 µM; a gift from Dr. Schinkel, University of Amsterdam, NL). Rhodamine 123 (10 µM), calcein-AM (10 µM) or [$^3$H] daunorubicin were then added for the indicated periods of time. The plates were shaken during both preincubation and incubation periods to reduce the effect of the aqueous boundary layer on drug accumulation. The cells were rapidly washed three times with ice-cold PBS to eliminate the extracellular drug, and then lyed in 100 µl 0.1 M NaOH or 1% Triton-X100. The amount of fluorescent substrates retained in the cells was determined in a Wallac F-Lite™ 2001 fluorescence plate reader with a 485 nm bandpass excitation/emission filter and accumulated fluorescence was expressed in arbitrary fluorescence units per well, whereas the radioactivity retained in the cells was measured using a β-scintillation counter (Pharmacia Wallac 1410).

Statistical Analysis

Results are expressed as the means±SEM and significant differences between groups determined by Student's t-test or ANOVA as appropriate. P<0.01 was considered significant.

Results

Immortalisation of Human Adult Brain Endothelial Cells

Endothelial cell colonies emerged from human brain cortical microvessel fragments by days 5-10 following isolation and seeding and reached confluence from days 25-35. At confluence, primary cultures of human brain endothelia exhibited spindle shaped morphology previously documented in brain endothelial cells derived from human (Dorovini-Zis et al. 1991) and other species (Abbott et al. 1992). Following lentiviral infection of preconfluent primary brain endothelial cell cultures in passage 0, several hundred parent cell lines of immortalized human brain microvessel endothelial cells were obtained by two subsequent rounds of limiting dilution cloning, from which one clonal population, named hCMEC/D3, was selected. The hCMEC/D3 cell line exhibited a non-transformed phenotype, grew preferentially on a collagen I substrate; and showed morphology similar to primary cultures of brain endothelial cells, with confluent monolayers of tightly packed elongated cells at confluence that exhibited contact inhibition. The hCMEC/D3 cell population stably displays the presence of nuclear SV40-T antigen protein and abundant amounts of nuclear and perinuclear hTERT protein by confocal microscopy.

The hCMEC/D3 cell line exhibits a diploid karyotype, without any major chromosomal rearrangements, both at passage 22 and passage 33, and its phenotype remained unchanged over more than one hundred population doublings (35 passages), without any sign of senescence, dedifferentiation or transformation. Whereas the primary culture required a medium enriched in multiple growth factors (bFGF, VEGF, IGF-1, EGF) plus serum and cells grew very slowly, the transduced hCMEC/D3 cells grow rapidly in EGM-2 medium and can be maintained with one-tenth the concentration of growth factors. Growth rates increased further in the presence of combinations of VEGF and EGF or bFGF and EGF. When the hCMEC/D3 cells were seeded on extracellular matrix Matrigel, they rapidly formed a branched network of vascular cords, a characteristic typical of primary endothelial cells, suggesting a normal capacity for angiogenesis. The hCMEC/D3 cells did not form any colonies in soft agar, by contrast with a human glioma cell line U87, used as a positive control, which grew multiple large colonies under the same conditions.

Figure 1:
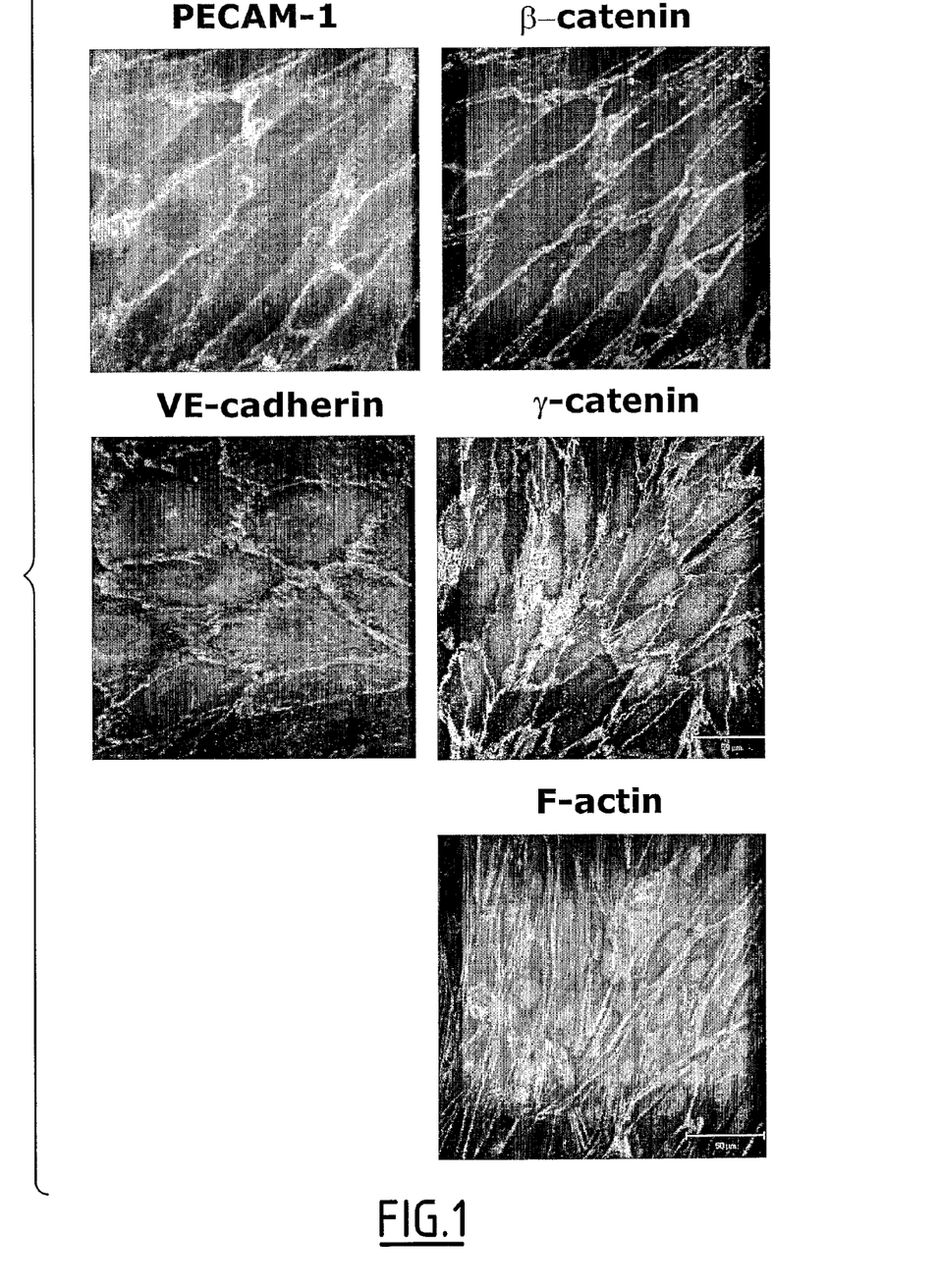
FIG. 1: Expression of junctional markers on plasma membrane of hCMEC/D3 cells. Confocal micrographs of confluent monolayers of hCMEC/D3 cells showing continuous staining at intercellular junctions with antibodies to PECAM-1, VE-cadherin gamma-catenin, beta-catenin. Phalloidin labelling of F-actin Magnification 630×.

The hCMEC/D3 cell line constitutively expresses many endothelial markers with the expected subcellular localization pattern: von Willebrand factor, appearing as large cytoplasmic granules, and PECAM-1, VE-cadherin, β- and γ-catenins, appearing as cellular junction-associated proteins (FIG. 1). In addition, F-actin was mostly localized at cell-cell junctions, as expected from cells with properly organized multi-protein complexes at adherens junctions (FIG. 1, lower panel). Altogether, these observations strongly suggest that the hCMEC/D3 cell line displays a phenotype close to that of normal primary endothelial cells. No change was detected in the junctional expression of VE-cadherin, β-catenin or any other tested endothelial marker from early passages to passage 33.

Expression of Leukocyte Adhesion Molecules and Chemokine Receptors

Figure 2:
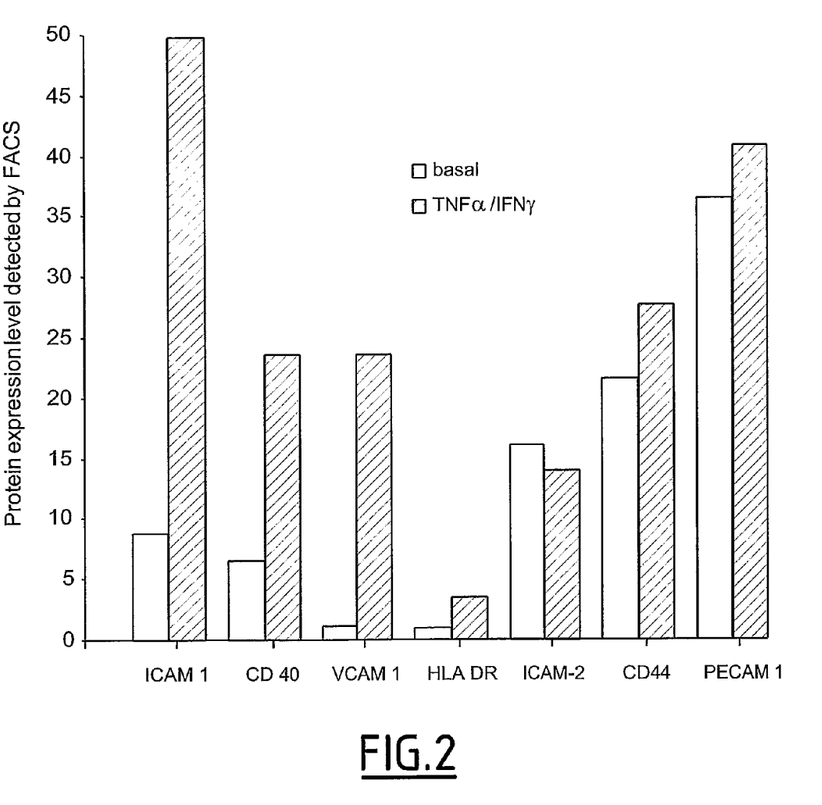
FIG. 2: Adhesion molecule expression on the plasma membrane of hCMEC/D3 cells. Histogram of FACS analysis data of adhesion molecule expression by hCMEC/D3 cells. Open bars represent basal expression, unstimulated; closed bars represent adhesion molecule expression following 24 hr stimulation with a combination of TNFα (100 U/ml) and IFNγ (100 U/ml), and cell staining with double antibody technique detailed in Materials and Methods. Values on the Y axis are in arbitrary fluorescence units, and represent the mean of 3 separate experiments in triplicate.

By FACS analysis, hCMEC/D3 cells were shown to express, in addition to PECAM, in particular PECAM-1 which is strongly expressed, the leukocyte adhesion molecules ICAM-2 and CD44 (FIG. 2) in a constitutive manner, as expected for differentiated endothelial cells. In addition, upon induction with inflammatory cytokines (TNF-α+IFN-γ) these cells expressed or increased expression of other adhesion molecules involved in leukocyte transmigration and/or antigen presentation. ICAM-1 and CD40 basal expression was low in confluent, unstimulated cells and was dramatically upregulated following a 24-hr treatment with 100 U/ml IFN-γ and 100 U/ml TNFα, whereas VCAM-1 and MHC-II expression were undetectable in non-treated cells but were strongly induced by the same cytokine treatment (FIG. 2). Moreover, cytokine-induced E-selectin expression could be easily detected by RT-PCR whereas unstimulated cells were negative for E-selectin expression. These findings correlate with a similar pattern of regulated expression of adhesion molecules previously reported with primary cultures of human brain endothelial cells (Wong and Dorovini-Zis 1992; Wong et al. 1999; Omani and Dorovini-Zis 2003). By contrast, hCMEC/D3 cells were not stained by non-endothelial markers, respectively: GFAP (astrocyte marker), CD69 (monocyte marker), DC-SIGN-1 (dendritic cell marker), or by DC-SIGN-2 which has been reported to be expressed only by some non-brain endothelial cells.

Multiple chemokines released by perivascular glial cells have been implicated in mediating the infiltration of leukocytes through the BBB into the CNS in a variety of neuroinflammatory conditions, either following receptor-mediated transcytosis to the luminal side of brain endothelium and/or by stimulation of signal transduction in endothelial cells. The FACS analysis revealed that hCMEC/D3 cells, similarly to human brain microvessels or primary cultures of human brain endothelial cells (Berger et al. 1999; Andjelkovic and Pachter 2000), express a variety of chemokine receptors: CXCR-1 to CXCR-5, CCR-3, -5, -6, whereas CCR-4, although expressed at low levels in primary human brain endothelium, could not be detected in hCMEC/D3 cells at first. However, further experiments showed that CCR-4 was indeed expressed by hCMEC/D3 cells. Neither primary human brain endothelial cells nor hCMEC/D3 expressed CCR1 or CCR2. Upon stimulation with TNFα and IFNγ, there was a slight increase in the expression of CXCR2, CXCR3 and CCR6 but not other chemokine receptors.

Figure 7:
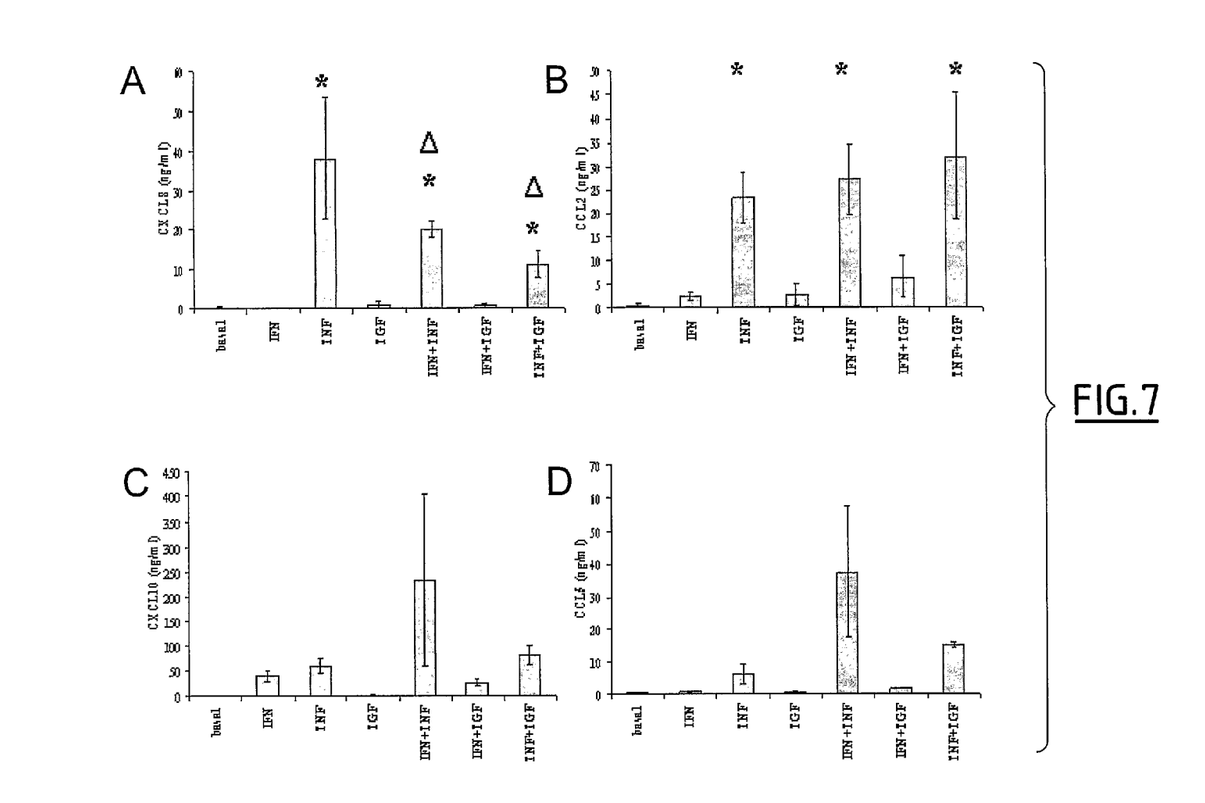
FIG. 7: Chemokine release into culture medium by hCMEC/D3 cells following stimulation by cytokines for 48 h. CXCL8 (A), CCL2 (B), CXCL10 (C) and CCL5 (D) release by hCMEC/D3 cells was assayed (vertical axis, ng/ml) following stimulation by respectively no cytokine (control, basal), IFN-γ, TNF-α, TGF-β, IFN-γ+TNF-α, IFN-γ+TGF-β, TNF-α+TGF-β (horizontal axis). * represents a significant difference (P<0.05) versus the control; Δ represents a significant difference (P<0.05) of sample treated with a combination of cytokines versus TNF-α treated sample.
Figure 8:
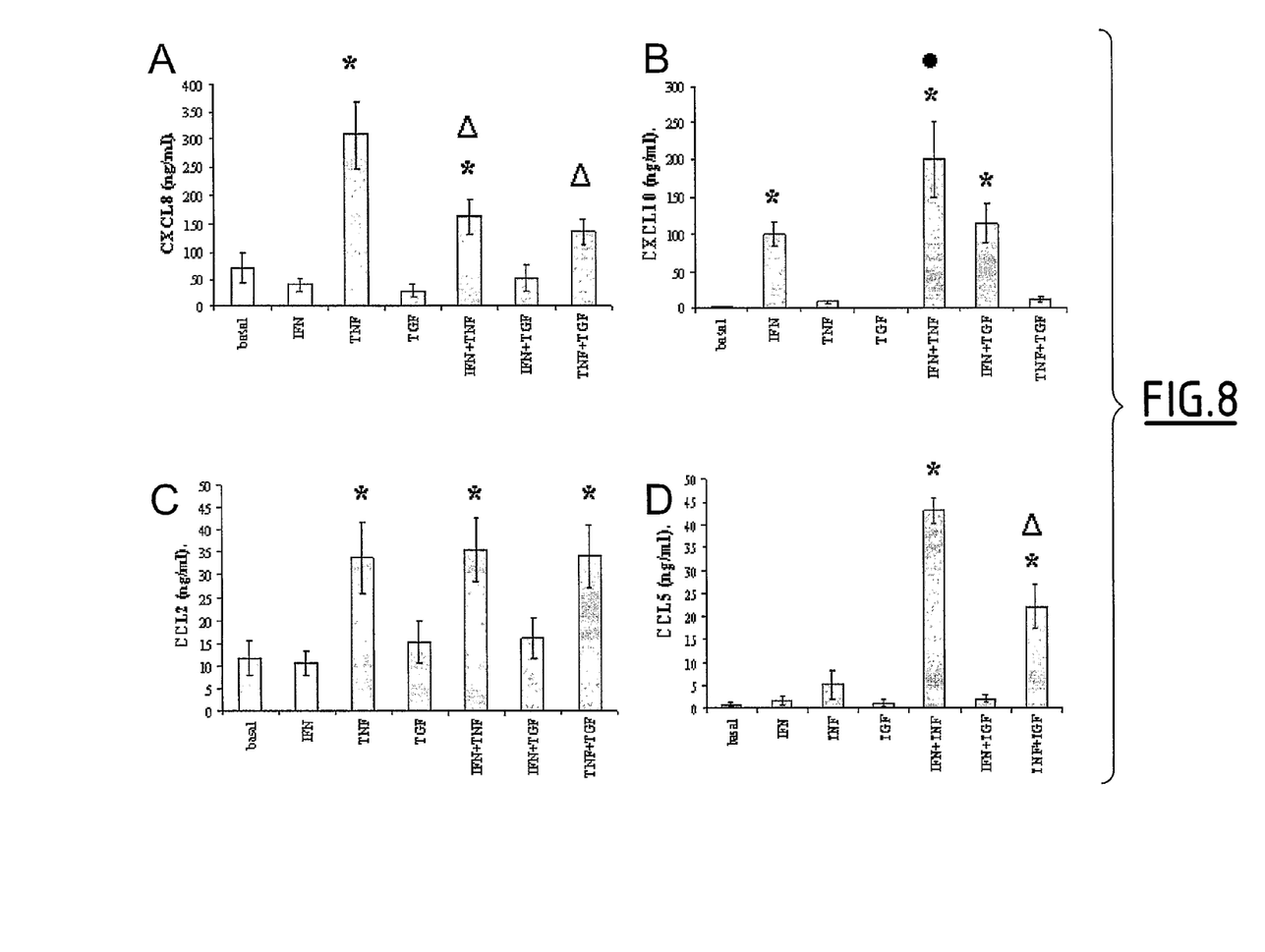
FIG. 8: Chemokine release into culture medium by human brain endothelial cells (HBEC) following stimulation by cytokines for 48 h. CXCL8 (A), CXCL10 (B), CCL2 (C) and CCL5 (D) release by HBEC was assayed (vertical axis, ng/ml) following stimulation by respectively no cytokine (control, basal), IFN-γ, TNF-α, TGF-β, IFN-γ+TNF-α, IFN-γ+TGF-β, TNF-α+TGF-β (horizontal axis). * represents a significant difference (P<0.05) versus the control; Δ represents a significant difference (P<0.05) of sample treated with a combination of cytokines versus TNF-α treated sample; ● represents a significant difference (P<0.05) of sample treated with a combination of cytokines versus IFN-γ treated sample.

Furthermore, the capacity of hCMEC/D3 cells to release chemokines (CXCL8, CCL2, CXCL10 and CCL5) in response to inflammatory cytokines (TNF-α, IFN-γ, TGF-β or a combination of them) has been assessed by the Inventors (FIG. 7). For comparison, primary cultures of human brain endothelial cells (HBEC, FIG. 8) were included in the same assay. Results indicate that hCMEC/D3 cells response to inflammatory stimuli is quite similar to that of primary human brain endothelial cells. These data complement the previous observation (FIG. 2) that hCMEC/D3 cells express a number of adhesion molecules, in a cytokine-modulated manner, which are known to be expressed at the surface of brain endothelium in situ, in inflammatory situations.

Expression of Tight Junction-Specific Markers—Drug Permeability

Figure 3:
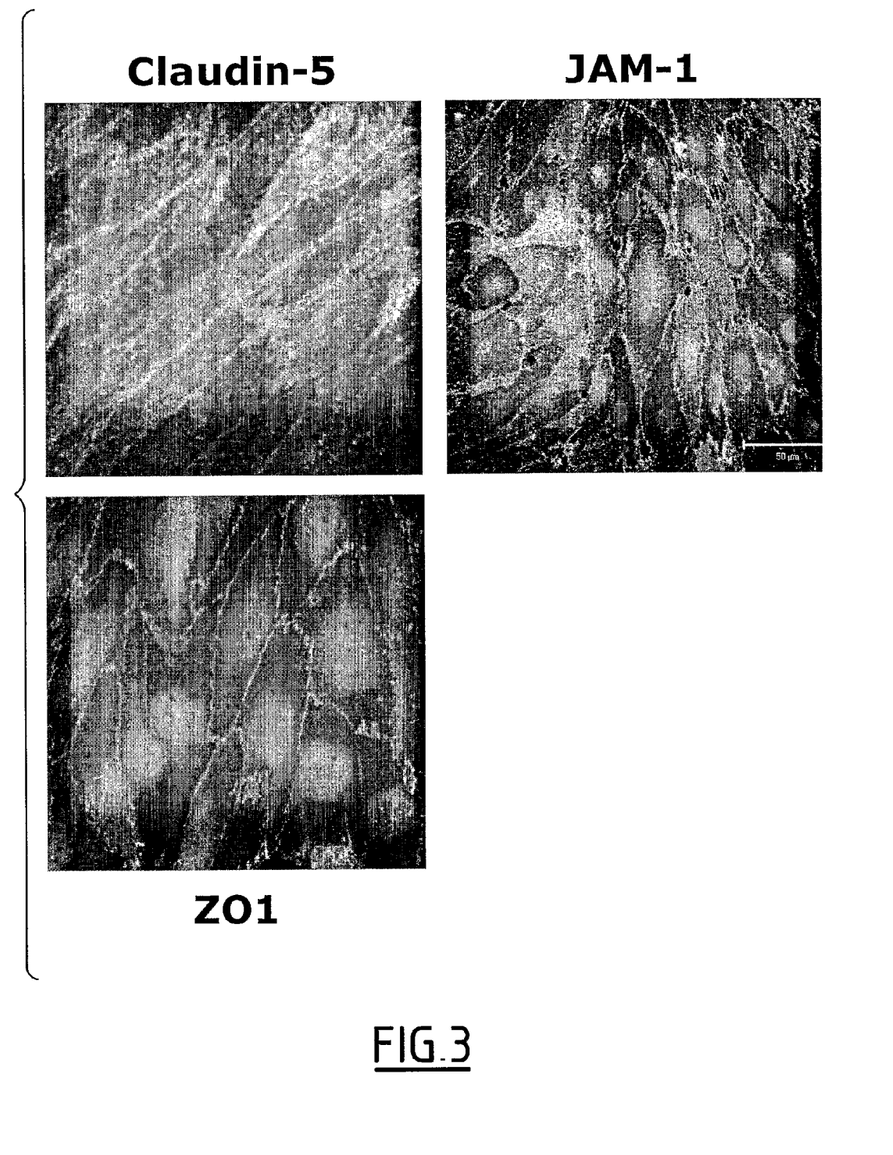
FIG. 3: Expression of junction-associated proteins by hCMEC/D3 cells. The junction-associated proteins claudin-5, JAM-1, ZO-1 and occludin were expressed in a continuous manner on the plasma membranes, at the intercellular junctions of confluent hCMEC/D3 cells. Confocal micrographs, magnification 630×.

Interestingly, the hCMEC/D3 cell line also displays expression of several tight-junction associated proteins. The submembranous tight junction-associated protein ZO-1 and the integral membrane protein JAM-1 are components of the BBB endothelium in vivo. Immunofluorescent detection of ZO-1 and JAM-A in hCMEC/D3 cells revealed the continuous expression of both markers at cell-cell contacts (FIG. 3). Junctional expression of occludin and claudin-5 was also observed (FIG. 3). As a negative control, the epithelium-selective claudin-1, which is not expressed by brain endothelium in situ, was not detected in hCMEC/D3 cells.

Figure 6:
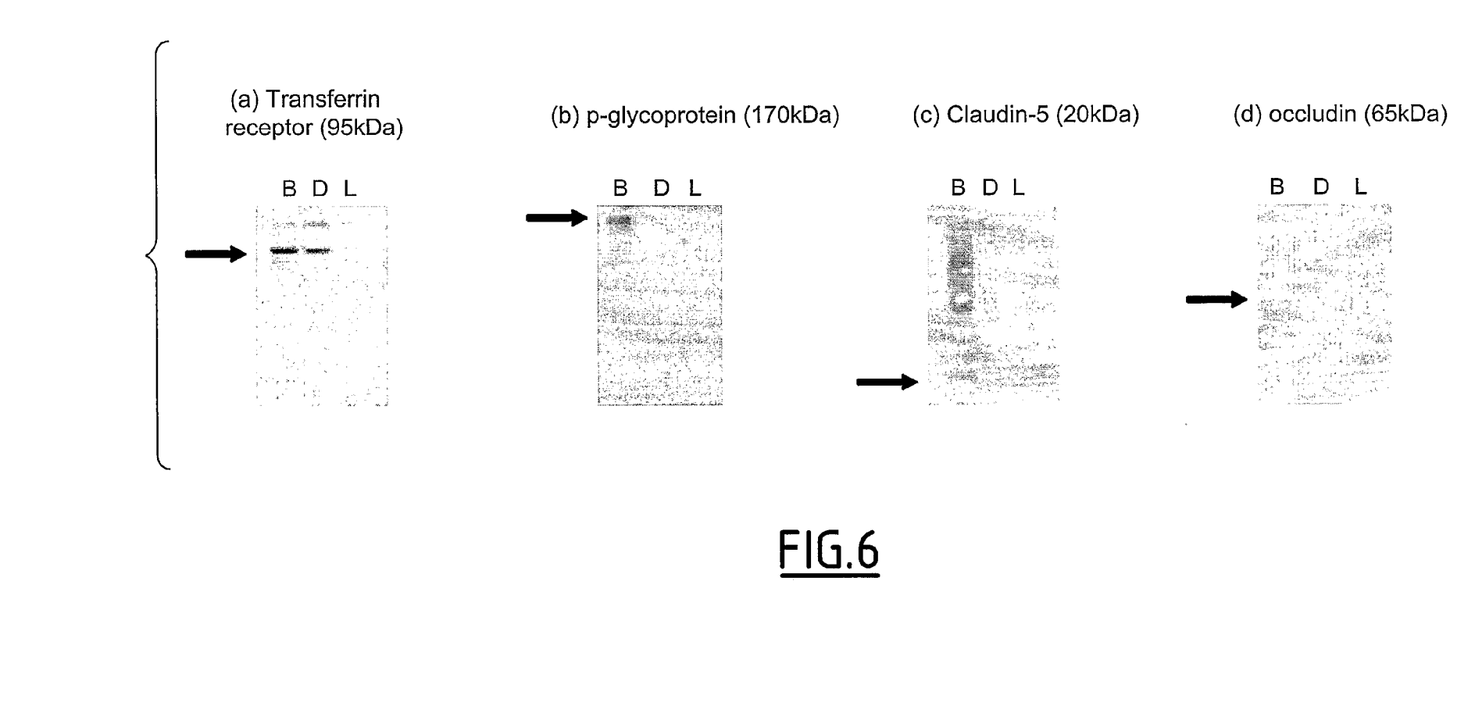
FIG. 6: Western blot analysis of cell lysates from hCMEC/D3 cells (in line B), and dermal (in line D) and lung (in line L) primary human cells with antibodies directed against the transferrin receptor (95 kDa) (A), the p-glycoprotein (170 kDa) (B), Claudin-5 (20 kda) (C) and Occludin (65 kDa) (D). Arrows indicate the expected molecular weight of each protein of interest.

Furthermore, western blot analysis confirmed the expression of claudin-5 and occludin, and evidenced the expression of the transferrin receptor and of the p-glycoprotein by hCMEC/D3 cells, four BBB markers, whereas lung microvascular endothelial cells (L) failed to express any of them and dermal microvascular endothelial cells (D) only expressed the transferrin receptor (FIG. 6). These results further demonstrate that hCMEC/D3 cells express a phenotype essentially similar to that of the BBB endothelium.

Confluent monolayers of the hCMEC/D3 cells line, grown to confluence on semi-permeable Transwell filters, exhibit restricted permeability to small molecules that are used as standard paracellular permeability markers.

TABLE 1

Permeability coefficients (Pe) of hCMEC/D3 cells:

| | Permeability coefficients ($\times 10^{-3}$ cm/min) | | | |
|---|---|---|---|---|
| | HCMEC/D3 | bovine co-culture model[1] | RBE4 rat cell line[2] | GPNT rat cell line[3] |
| [14C]-sucrose | 1.654 ± 0.175 | 0.75 | 4.8 | 7.37 |
| [3H]-inulin | 0.360 ± 0.027 | 0.37 | 1.3 | Nd |

| | Permeability coefficients ($\times 10^{-3}$ cm/min) | | | |
|---|---|---|---|---|
| FITC-Dextrans (kDa) | HCMEC/D3 | GPNT rat cell line | bovine brain endothelial cells (mono-cultures) | |
| 4 | 0.325 | 0.975 | 0.434[4] | 0.370[5] |
| 40 | 0.027 | 0.114 | 0.046[4] | n.d. |
| 70 | 0.013 | 0.053 | 0.008[4] | 0.126[5] |

[1]Cecchelli et al., 1999
[2]Rist et al., 1997
[3]Romero et al., 2000
[4]van Bree et al., 1988
[5]Mark and Miller, 1999

As shown in Table 1 (upper panel), permeability coefficients of hCMEC/D3 cells for [$^{14}$C]-sucrose (MW 300 Da) and [$^3$H]-inulin (MW 4000 Da), well known markers of paracellular permeability, were: 1.65±0.17 $10^{-3}$ cm/min and 0.36±0.03 $10^{-3}$ cm/min, respectively. Compared with permeability values reported using the reference BBB in vitro model constituted by co-cultures of bovine brain microvessel endothelial cells and rat glial cells (Cecchelli et al. 1999), inulin permeability through hCMEC/D3 cells was similar (0.36 vs $0.37 \times 10^{-3}$ cm/min), while sucrose permeability was higher (1.65 vs $0.75 \times 10^{-3}$ cm/min), as shown in Table 1. These permeability values are, however, much lower than those previously reported for the rat brain endothelial cell lines, RBE4 and GPNT (around $4-7 \times 10^{-3}$ cm/min for sucrose and $1.3 \times 10^{-3}$ cm/min for inulin) (Table 1). In addition, permeability to a series of dextrans of increasing molecular size (4 to 70 kDa) further confirmed that hCMEC/D3 monolayers exert a much more stringent restriction than do GPNT monolayers on the trans-endothelial passage of both low-MW and high-MW molecules (Table 1, lower panel). However, transendothelial electric resistance (TEER) was constantly found to remain at low levels (<40 Ω·cm$^2$) under the same culture conditions, reflecting a high ionic permeability. Furthermore, supplementary data indicate that treatments with a cAMP-elevating agent (1 µM of chlorophenylthio-cAMP) and culture medium conditioned by primary human astrocytes (50%), described previously for their ability to decrease endothelial permeability, failed to significantly increase the TEER value.

The permeability of hCMEC/D3 cells could be further restricted using modified growth conditions. Briefly, cells where seeded at the same density as before in EBM-2 basal medium supplemented with 2.5% FBS, hydrocortisone, Hepes (10 mM; pH 7.4) and basic FGF (but not VEGF, IGF-1 and EGF) and half of the medium was changed at day 4 in both upper and lower compartments; permeability assays were then performed at day 7. The results show that [$^{14}$C]-sucrose permeability was significantly reduced to 1.03±0.07 $10^{-3}$ cm/min and that [$^3$H]-inulin permeability was also reduced to 0.30±0.07 $10^{-3}$ cm/min.

In addition, permeability of Lucifer Yellow (Sigma, USA), an alternative paracellular permeability fluorescent standard of about 450 Da, was measured: the result (0.53±0.10 $10^{-3}$ cm/min) is in agreement with the slightly higher molecular weight of this compound than that of sucrose. Because it is easier to use than radioactively labelled sucrose, Lucifer Yellow can be routinely used as an internal standard for further permeability assays.

These observations are consistent with a differentiation of hCMEC/D3 towards a BBB phenotype.

In order to further assess whether the hCMEC/D3 cell line could be considered as a valuable in vitro model of BBB, the inventors carried out in vitro/in vivo comparisons for several standard compounds with different physico-chemical properties and increasing hydrophobicity: sucrose, morphine-6-glucuronide, inulin, vincristine, colchicine, prazosin, diazepam, and imipramine. Permeability coefficients (Pe in cm/min) were correlated with in vivo permeability data (expressed as Kin transport constant values) obtained by brain perfusion of adult rats, which is considered quantitatively similar to human values.

TABLE 2

Permeability coefficient and Kin transport constant values for standard drugs:

| | In vitro Pe (cm/min) | In vivo Kin |
|---|---|---|
| Diazepam | 3.62 | 45 |
| Prazosin | 3.02 | 0.96 |
| M6G (morphine 6 glucuronide) | 0.037 | 0.03 |
| Colchicine | 1.58 | 0.28 |
| Vincristine | 0.68 | 0.06 |
| Inuline | 0.3 | |
| Sucrose | 1.29 | |

Figure 4:
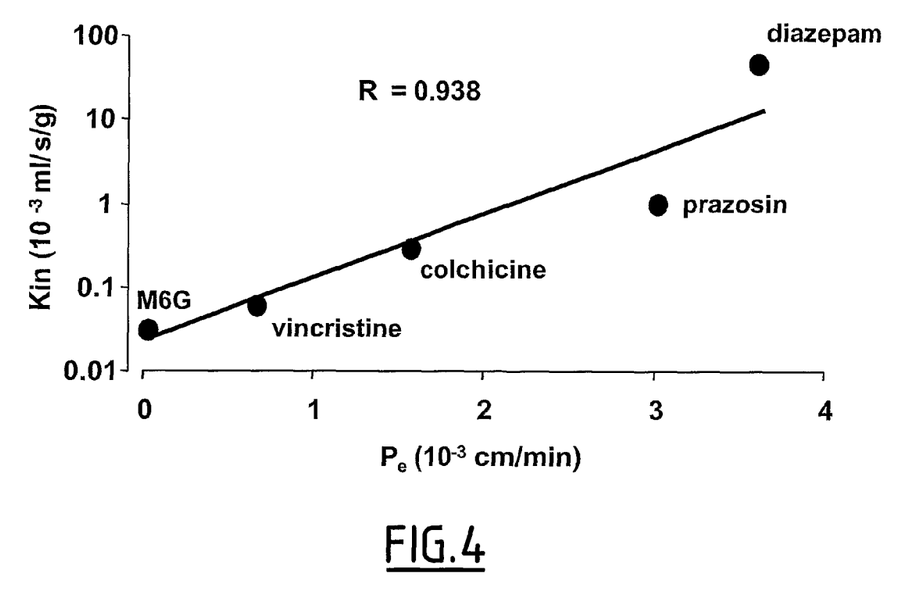
FIG. 4: Correlations between in vitro permeability of confluent monolayers of hCMEC/D3 cells and reported in vivo BBB permeability for a variety of chemical substances and drugs.

It must be noted that because imipramine was partly retained on the filters by hydrophobic interactions as previously reported (Cecchelli et al. 1999), imipramine values were not included in the regression analysis. As shown in FIG. 4, the results demonstrate a good correlation (r=0.938) between in vitro and in vivo data.

For comparison, similar experiments were performed with human umbilical vein endothelial cells (HUVECs), which are not expected to form a tight diffusion barrier and with the rat brain endothelial cell line GPNT (Romero et al. 2003). Permeability data for vincristine, colchicine, prazosin, and diazepam showed a poor correlation between in vivo brain perfusion values and in vitro data (R=0.881) with HUVECs, whereas a good correlation (R=0.965) was observed with GPNT cells. Furthermore, a good correlation between hCMEC/D3 and GPNT permeability data (R=0.990) was found, but no correlation between hCMEC/D3 and HUVEC permeability data (R=0.628) could be found. These observations clearly indicate that a good correlation between in vitro and in vivo BBB permeability data could only be achieved with monolayers of brain endothelial cells.

These observations clearly point to the hCMEC/D3 cell line as a potential in vitro model of human BBB, in particular for hydrophobic drugs and for hydrophilic molecules of molecular weight higher than sucrose.

Expression and Functionality of Multidrug Resistance Proteins

In conjunction with the presence of inter-endothelial tight junctions, BBB endothelium is characterized by a highly restrictive permeability to hydrophobic molecules resulting from the expression of several multidrug resistance proteins of the ATP-binding cassette (ABC) transporter family that function as non-selective drug export pumps and protect the CNS from a very large panel of potentially harmful hydrophobic compounds. Among these efflux pumps are P-gp (also called MDR1 or ABCB1) (Schinkel 1999; Begley 2004), the multidrug resistance-associated protein-1 (MRP1 or ABCC1) (Begley 2004) and the more recently described breast cancer resistance protein (BCRP or ABCG2) (Eisenblatter et al. 2003; Zhang et al. 2003), pumps that exhibit distinct, but overlapping substrate preferences. All three transcripts were detected in hCMEC/D3 cells, as well as in primary cultures of human brain endothelial cells. In addition, the inventors also detected the MRP5-encoding transcript both in hCMEC/D3 cells and in primary human brain endothelial cells, as previously detected in bovine brain endothelial cells (Berezowski et al. 2004). Protein expression of P-gp, MRP1 and BCRP was further confirmed by western blot analysis: these efflux pumps were detected as 170 kDa, 190 kDa and 70 kDa proteins, respectively, as expected from previous reports (Regina et al. 1999; Zhang et al. 2003). As control, primary cultures of human astrocytes were shown not to express MRP1 or BCRP, but to express low levels of P-gp, as described (Pardridge).

Figure 5:
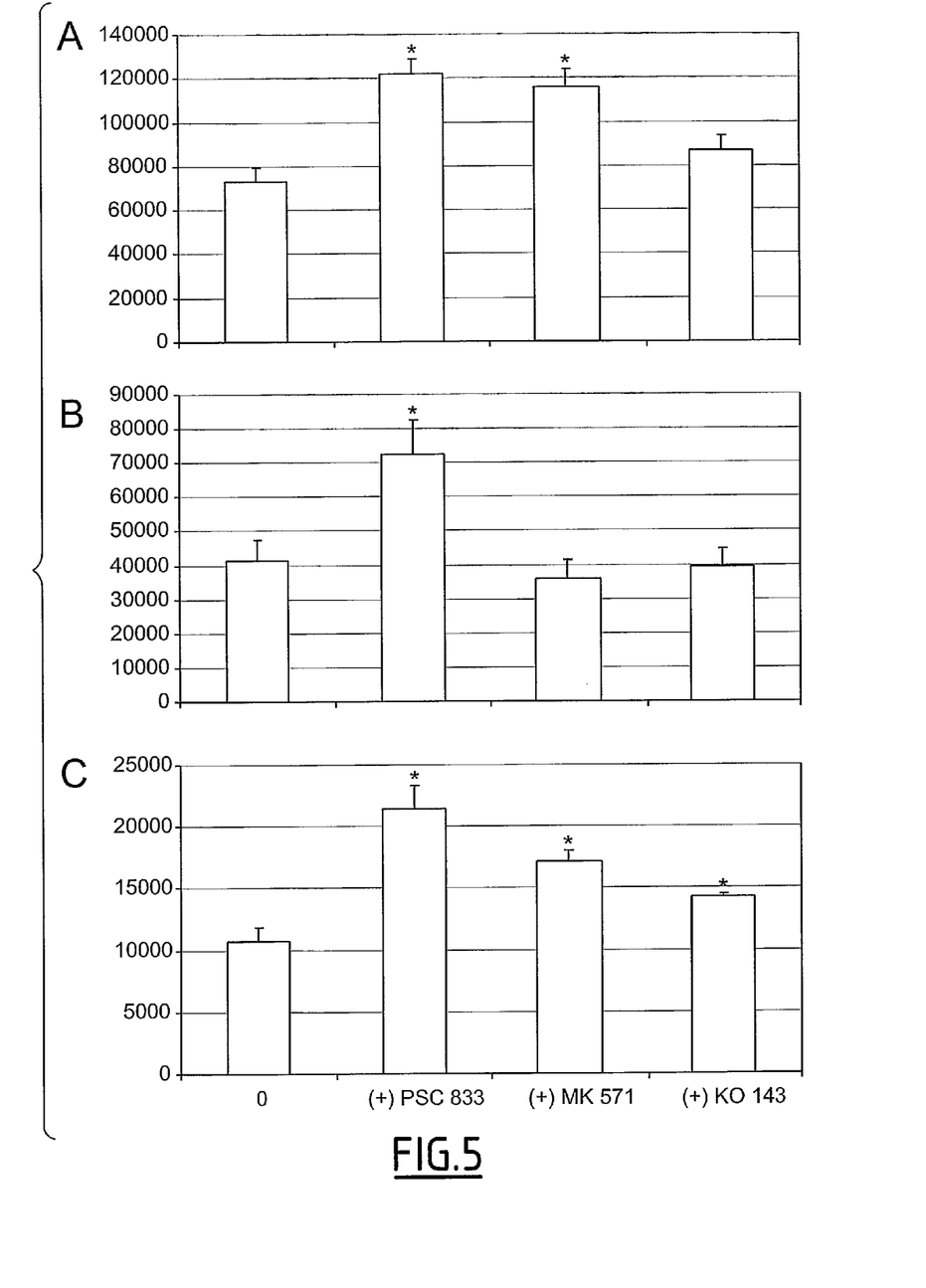
FIG. 5: Functionality of ABC efflux pumps in hCMEC/D3 cells. Uptake of calcein-AM, a P-gp and MRP1 substrate (A), rhodamine 123, a P-gp and BCRP substrate (B) or [$^3$H] daunorubicin, a shared substrate of all three P-gp, MRP1 and BCRP transporters (C), in the absence or presence of specific P-gp, MRP1 or BCRP inhibitor, respectively PSC-833 (10 μM), MK-571 (10 μM) or KO-143 (1 μM), as indicated. Three independent experiments were performed; results from one representative experiment in triplicates are presented, expressed in arbitrary units of fluorescence (A, B) or in dpm (C). * indicates that uptake in the presence of inhibitor is significantly different (p<0.01) from control (0).

The functionality of these pumps was then evaluated by assessing the uptake by hCMEC/D3 monolayers of drugs that are known as substrates of at least two ABC transporters: calcein-AM, a P-gp and MRP1 substrate (FIG. 5A), (Feller et al. 1995); rhodamine 123, a P-gp and BCRP substrate (FIG. 5B), [$^3$H] daunorubicin, a shared substrate of all three P-gp, MRP1 and BCRP transporters (FIG. 5C), in the absence or presence of specific inhibitors: PSC-833 (10 µM), MK-571 (10 µM) or KO-143 (1 µM) for P-gp, MRP1 and BCRP, respectively. As shown in FIG. 5, PSC-833 markedly increased calcein-AM, rhodamine 123 and daunorubicin uptake by hCMEC/D3 cells, indicating that P-gp was highly active in these cells. The selective MRP1 blocker MK-571 significantly increased calcein-AM and daunorubicin uptake, but not rhodamine 123 uptake: this result, in good agreement with the reported selectivity of these substrates, suggests that MRP1 is functional in hCMEC/D3 cells. Finally, KO-143, a specific inhibitor of BCRP significantly increased [$^3$H] daunorubicin only, although to a limited extent, showing that this ABC transporter is moderately active and/or expressed in hCMEC/D3 cells, in agreement with a recent report on primary cultures of human brain endothelial cells (Zhang et al., 2003; KO-143 did not significantly affect rhodamine 123 uptake, suggesting, as recently proposed (Robey et al., 2001), that rhodamine 123 uptake is not sensitive enough in detecting BCRP activity. Taken together, these results demonstrate that hCMEC/D3 cells express three ABC efflux transporters (P-gp, MRP1 and BCRP) known to be expressed by brain endothelium and that all three are functional.

In conclusion, these results indicate that the human brain endothelial cell line hCMEC/D3 recapitulates most of the unique properties of the BBB, even without co-culture with glial cells. The hCMEC/D3 cell line represents the first available in vitro model of human BBB. It is particularly useful as a model for studying the biology of human brain endothelium in the context of neuro-inflammatory or infectious diseases, to unravel the mechanisms of CNS infiltration by human immune cells or infection by human-specific viral pathogens (Couraud et al. 2003). On the basis of the restricted permeability of hCMEC/D3 monolayers to a variety of compounds, in good correlation with in vivo results, and expression of the three major ABC efflux transporters known to be present at the BBB, the hCMEC/D3 cell line constitutes a unique human in vitro model for large scale screening of CNS drug candidates.

REFERENCES

Abbott, N. J., C. C. Hughes, et al. (1992). "Development and characterisation of a rat brain capillary endothelial culture: towards an in vitro blood-brain barrier." *J Cell Sci* 103(Pt 1): 23-37

Abbott, N. J., P. O. Couraud, et al. (1995). Studies of an immortalized brain endothelial cell line: characterization, permeability and transport. *New Concepts of a blood-brain barrier*. J. Greenwood, DJ Begley, M. Segal and S. Lightman. New-York, Plenum Press.

Andjelkovic, A. V. and J. S. Pachter (2000). "Characterization of binding sites for chemokines MCP-1 and MIP-1alpha on human brain microvessels." *J Neurochem* 75(5): 1898-906.

Bauer, B., Miller, D. S., Fricker, G. (2003) Compound profiling for P-glycoprotein at the blood-brain barrier using a microplate screening system. *Pharm Res.* 20 (8): 1170-76

Begley, D. J. (2004). "ABC transporters and the blood-brain barrier." *Curr Pharm Des* 10(12): 1295-312.

Berezowski, V., C. Landry, et al. (2004). "Contribution of glial cells and pericytes to the mRNA profiles of P-glycoprotein and multidrug resistance-associated proteins in an in vitro model of the blood-brain barrier." *Brain Res* 1018 (1): 1-9.

Berger, O., X. Gan, et al. (1999). "CXC and CC chemokine receptors on coronary and brain endothelia" *Mol Med* 5(12): 795-805.

Biegel, D., D. D. Spencer, et al. (1995). "Isolation and culture of human brain microvessel endothelial cells for the study of blood-brain barrier properties in vitro." *Brain Res* 692 (1-2): 183-9.

Bodnar, A. G., M. Ouellette, et al. (1998). "Extension of life-span by introduction of telomerase into normal human cells." *Science* 279(5349): 349-52

Cecchelli, R., B. Dehouck, et al. (1999). "In vitro model for evaluating drug transport across the blood-brain barrier." *Adv Drug Deliv Rev* 36(2-3): 165-178.

Cisternino, S., C. Rousselle, et al. (2001). "Screening of multidrug-resistance sensitive drugs by in situ brain perfusion in P-glycoprotein-deficient mice." *Pharm Res* 18(2): 183-90.

Cisternino, S., C. Rousselle, et al. (2003). "In vivo saturation of the transport of vinblastine and colchicine by P-glycoprotein at the rat blood-brain barrier." *Pharm Res* 20(10): 1607-11.

Cisternino, S., C. Rousselle, et al. (2004). "In situ transport of vinblastine and selected P-glycoprotein substrates: implications for drug-drug interactions at the mouse blood-brain barrier." *Pharm Res* 21(8): 1382-9

Couraud, P. O., X. Nassif, et al. (2003). "Mechanisms of infiltration of immune cells, bacteria and viruses through brain endothelium." *Adv Mol Cell Biol* 31: 255-268.

Dehouck, M. P., P. Jolliet-Riant, et al. (1992). "Drug transfer across the blood-brain barrier: correlation between in vitro and in vivo models." *J. Neurochem*. (58): 1790-1797.

Dorovini-Zis, K., R. Prameya, et al. (1991). "Culture and characterization of microvascular endothelial cells derived from human brain." *Lab Invest* 64(3): 425-36.

Eisenblatter, T., S. Huwel, et al. (2003). "Characterisation of the brain multidrug resistance protein (BMDP/ABCG2/BCRP) expressed at the blood-brain barrier." *Brain Res* 971(2): 221-31.

Engelbertz, C., D. Korte, et al. (2000). The development of in vitro models for the blood-brain and blood-CSF barriers. *The Blood-Brain Barrier and Drug Delivery to the CNS*. D. Begley, Bradbury, M. W. and Kreuter, J. New York, Marcel Dekker: 33-63.

Feller, N., C. M. Kuiper, et al. (1995). "Functional detection of MDR1/P170 and MRP/P190-mediated multidrug resistance in tumour cells by flow cytometry." *Br J Cancer* 72(3): 543-9.

Flynn, G., S. Maru, et al. (2003). "Regulation of chemokine receptor expression in human microglia and astrocytes." *J Neuroimmunol* 136(1-2): 84

Gu, X., J. Zhang, et al. (2003). "Brain and retinal vascular endothelial cells with extended life span established by ectopic expression of telomerase." *Invest Opthalmol Vis Sci* 44(7): 3219-25.

Gumbleton and Audus, (2001) Journal of pharmaceutical Sciences, vol. 90, No. 11

Gutmann, H., M. Torok, et al. (1999). "Modulation of multidrug resistance protein expression in porcine brain capillary endothelial cells in vitro." *Drug Metab Dispos* 27(8): 937-41.

Joo, F. (1993). "The blood-brain barrier in vitro: the second decade [see comments]." *Neurochem Int* 23(6): 499-521.

Murphy, P. R., Y. Sato, et al. (1992). "Phosphorothioate antisense oligonucleotides against basic fibroblast growth factor inhibit anchorage-dependent and anchorage-independent growth of a malignant glioblastoma cell line." *Mol Endocrinol* 6(6): 877-84

Muruganandam et al., (1997) the FASEB Journal vol. 11, 1187-1197

Nare, B., R. K. Prichard, et al. (1994). "Characterization of rhodamine 123 binding to P-glycoprotein in human multidrug-resistant cells." *Mol Pharmacol* 45(6): 1145-52.

Nitta, T., M. Hata, et al. (2003). "Size-selective loosening of the blood-brain barrier in claudin-5-deficient mice." *J Cell Biol* 161(3): 653-60.

O'Hare, M. J., J. Bond, et al. (2001). "Conditional immortalization of freshly isolated human mammary fibroblasts and endothelial cells." *Proc Natl Acad Sci USA* 98(2): 646-51

Omani, K. M. and K. Dorovini-Zis (2003). "CD40 expressed by human brain endothelial cells regulate CD4+ T cell adhesion to endothelium." *J Neuroimmunol* 134: 166-178.

Prudhomme J, Sherman I, Land K, Moses A, Stenglein S and Nelson JA (1986) Studies of *plasmodium falciparum* cytoadherence using immortalized human brain capillary endothelial cells. *Int J Parasitol* 26:647-655.)

Regina, A., I. A. Romero, et al. (1999). "Dexamethasone regulation of P-glycoprotein activity in an immortalized rat brain endothelial cell line, GPNT." *J Neurochem* 73(5): 1954-63.

Rist, R. J., I. A. Romero, et al. (1997). "F-actin cytoskeleton and sucrose permeability of immortalised rat brain microvascular endothelial cell monolayers: effects of cyclic AMP and astrocytic factors." *Brain Res* 768: 10-18.

Robey, R. W., Y. Honjo, et al. (2001). "A functional assay for detection of the mitoxantrone resistance protein, MXR (ABCG2)." *Biochim Biophys Acta* 1512(2): 171-82.

Romero, I. A., M. C. Prevost, et al. (2000). "Interactions between brain endothelial cells and human T-cell leukemia virus type 1-infected lymphocytes: mechanisms of viral entry into the central nervous system." *J Virol* 74(13): 6021-30.

Romero, I. A., Radewicz, K. et al. (2003) "Changes in cytoskeletal and tight junctional proteins correlate with decreased permeability induced by dexamethasone in cultured rat brain endothelial cells." *Neurosci Lett* 344: 112-116.

Rubin, L. L., D. E. Hall, et al. (1991). "A cell culture model of the blood-brain barrier." *J Cell Biol* 115(6): 1725-35.

Safaa Ibrahim et al. JPET 295:1276-1283, 2000

Saitou, M., K. Fujimoto, et al. (1998). "Occludin-deficient embryonic stem cells can differentiate into polarized epithelial cells bearing tight junctions."*J Cell Biol* 141(2): 397-408.

Salmon, P., J. Oberholzer, et al. (2000). "Reversible immortalization of human primary cells by lentivector-mediated transfer of specific genes." *Mol Ther* 2(4): 404-14.

Schinkel, A. H. (1999). "P-glycoprotein, a gatekeeper in the blood-brain barrier." *Adv Drug Delivery Rev* 36: 179-194.

Schwab, D., H. Fischer, et al. (2003). "Comparison of in vitro P-glycoprotein screening assays: recommendations for their use in drug discovery." *J Med Chem* 46(9): 1716-25.

Seetharaman, S., M. A. Barrand, et al. (1998). "Multidrug resistance-related transport proteins in isolated human brain microvessels and in cells cultured from these isolates." *J Neurochem* 70(3): 1151-9.

Stins, M. F., F. Gilles, et al. (1997). "Selective expression of adhesion molecules on human brain microvascular endothelial cells." *J Neuroimmunol* 76(1-2): 81-90.

Tsukita, S, and M. Furuse (1999). "Occludin and claudins in tight-junction strands: leading or supporting players?" *Trends Cell Biol* 9(7): 268-73.

van Bree, J. B., A. G. de Boer, et al. (1988). "Characterization of an "in vitro" blood-brain barrier: effects of molecular size and lipophilicity on cerebrovascular endothelial transport rates of drugs." *J Pharmacol Exp Ther* 247(3): 1233-9

Wolburg, H. and A. Lippoldt (2002). "Tight junctions of the blood-brain barrier: development, composition and regulation." *Vasc Pharm* 38: 323-337.

Wolburg, H., K. Wolburg-Buchholz, et al. (2003). "Localization of claudin-3 in tight junctions of the blood-brain barrier is selectively lost during experimental autoimmune encephalomyelitis and human glioblastoma multiforme." *Acta Neuropathol* (*Berl*) 105(6): 586-92. Epub 2003 Feb. 25.

Wong, D. and K. Dorovini-Zis (1992). "Upregulation of intercellular adhesion molecule-1 (ICAM-1) expression in primary cultures of human brain microvessel endothelial cells by cytokines and lipopolysaccharide." *J Neuroimmunol* 39(1-2): 11-21.

Wong, D., R. Prameya, et al. (1999). "In vitro adhesion and migration of T lymphocytes across monolayers of human brain microvessel endothelial cells: regulation by ICAM-1, VCAM-1, E-selectin and PECAM-1." *J Neuropathol Exp Neurol* 58(2): 138-52.

Yamazaki, M., W. E. Neway, et al. (2001). "In vitro substrate identification studies for p-glycoprotein-mediated transport: species difference and predictability of in vivo results." *J Pharmacol Exp Ther* 296(3): 723-35.

Yang, J., E. Chang, et al. (1999). "Human endothelial cell life extension by telomerase expression." *J Biol Chem* 274(37): 26141-8

Zhang, W., J. Mojsilovic-Petrovic, et al. (2003). "The expression and functional characterization of ABCG2 in brain endothelial cells and vessels."*Faseb J* 17(14): 2085-7. Epub 2003 Sep. 4

Zennou, V., C. Petit, et al. (2000). "HIV-1 genome nuclear import is mediated by a central DNA flap." *Cell* 101(2): 173-85.

Zlokovic, B., V. (2004) Clearing amyloid through the blood-brain barrier. *J. Neurochem.* 89: 807-811.

The invention claimed is:

1. An immortalized human brain endothelial cell line that has a stable, non-transformed phenotype deposited at CNCM (Institut Pasteur) on Oct. 7, 2004 under deposit number No. I-3308.

2. One or more cells from the cell line of claim 1.

3. A method of measuring blood brain barrier permeability of a test substance, which method comprises:
   providing cells of claim 2 in one or more confluent monolayer(s);
   incubating said test substance with the confluent monolayer(s); and
   measuring the amount of said test substance permeated across the confluent monolayer(s).

4. The method of claim 3, wherein the amount of said test compound permeated across the confluent monolayer(s) is measured by passive diffusion or active transport.

5. A method for determining the toxicity of a test substance toward the blood brain barrier, which method comprises incubating said test substance with cells of claim 2 and assessing the viability of the cells.

* * * * *